(12) United States Patent
Mohr

(10) Patent No.: US 9,895,521 B2
(45) Date of Patent: Feb. 20, 2018

(54) TRANSDERMAL THERAPEUTIC SYSTEM WITH PRESSURE GENERATING DEVICE

(71) Applicant: LTS LOHMANN THERAPIE-SYSTEME AG, Andernach (DE)

(72) Inventor: Patrick Mohr, Bad Breisig (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 118 days.

(21) Appl. No.: 15/042,493

(22) Filed: Feb. 12, 2016

(65) Prior Publication Data

US 2016/0158515 A1    Jun. 9, 2016

Related U.S. Application Data

(63) Continuation-in-part of application No. PCT/EP2014/067238, filed on Aug. 12, 2014.

(30) Foreign Application Priority Data

Aug. 23, 2013 (EP) .................................... 13181516

(51) Int. Cl.
*A61M 37/00* (2006.01)
*A61M 5/145* (2006.01)

(52) U.S. Cl.
CPC .... *A61M 37/0015* (2013.01); *A61M 5/14593* (2013.01); *A61M 2037/0023* (2013.01)

(58) Field of Classification Search
CPC .......... A61M 37/0015; A61M 5/14593; A61M 2037/0023
See application file for complete search history.

(56) References Cited

U.S. PATENT DOCUMENTS 5,848,991 A    12/1998  Gross et al.
6,611,707 B1   8/2003   Prausnitz et al.
(Continued)

FOREIGN PATENT DOCUMENTS

DE    WO 2013/131643 A2    9/2013
KR               WO A2    6/2011
      2011/071/071287

OTHER PUBLICATIONS

The English translation of International Search Report for the corresponding international application PCT/EP2014/067238, dated Nov. 20 2014 (3 pages).

*Primary Examiner* — Emily Schmidt
*Assistant Examiner* — Amber Stiles
(74) *Attorney, Agent, or Firm* — R. S. Lombard

(57) ABSTRACT

A transdermal therapeutic system with a system support, at least one advancing element which is embedded into the system support, and at least one active ingredient reservoir which can be elastically deformed at least in some regions and which is embedded into the advancing element. On the application side of the transdermal therapeutic system, the system support surrounds the advancing element, and the advancing element surrounds the active ingredient reservoir. The advancing element comprises a swelling body which can be expanded by means of a liquid intake. The system support is designed to be rigid at least in some regions. A transdermal therapeutic system is developed which enhances the effect of the advancing element.

9 Claims, 2 Drawing Sheets

(56) References Cited

U.S. PATENT DOCUMENTS

| | | | |
|---|---|---|---|
| 2006/0047242 A1* | 3/2006 | Laurent ................ | A61B 17/205 604/46 |
| 2008/0269685 A1* | 10/2008 | Singh ................... | A61K 9/0021 604/173 |
| 2011/0087195 A1* | 4/2011 | Uhland ............. | A61M 37/0015 604/515 |
| 2011/0172601 A1 | 7/2011 | Beebe et al. | |
| 2011/0172637 A1* | 7/2011 | Moga ................ | A61M 5/14248 604/506 |

* cited by examiner

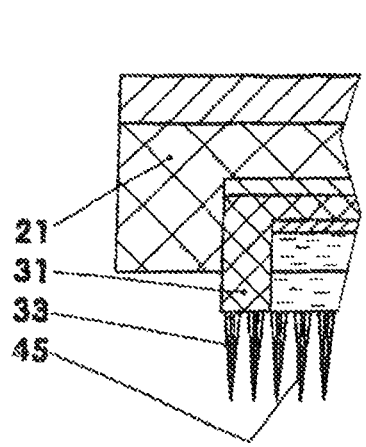
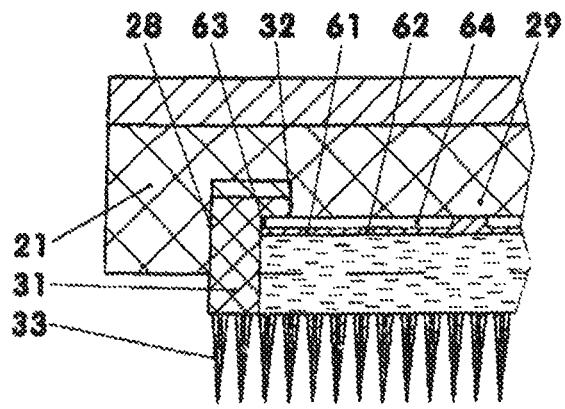
Fig. 4    Fig. 5
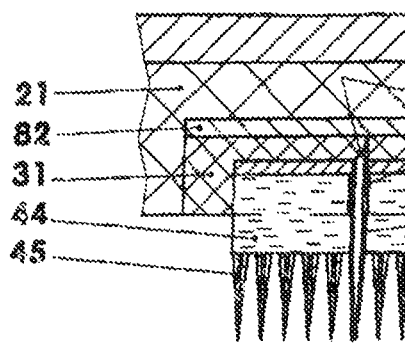
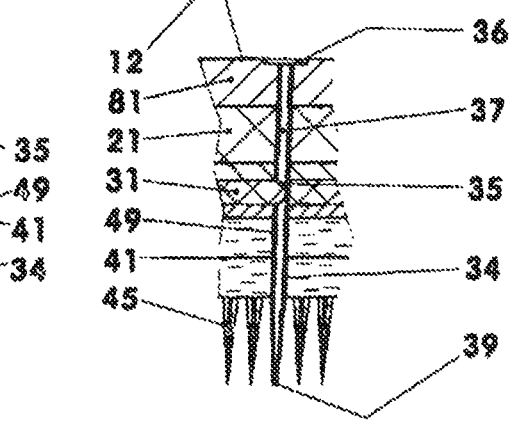
Fig. 6    Fig. 7
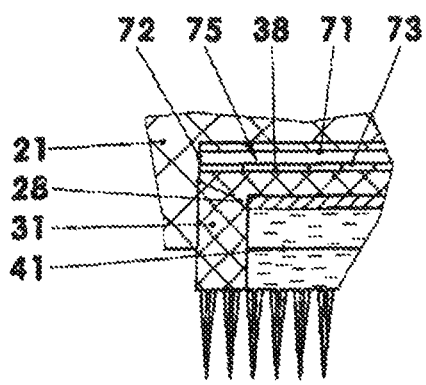
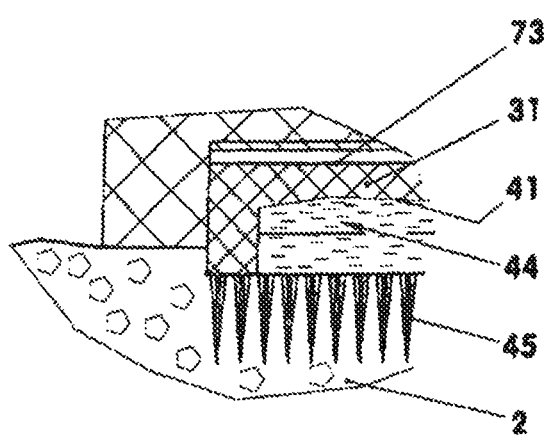
Fig. 8    Fig. 9

TRANSDERMAL THERAPEUTIC SYSTEM WITH PRESSURE GENERATING DEVICE

CROSS-REFERENCE TO RELATED APPLICATIONS

This is a continuation-in-part application of pending international application PCT/EP2014/067238 filed Aug. 12, 2014, and claiming the priority of European application No. 13181516.9 filed Aug. 23, 2013. The said International application PCT/EP2014/067238 and European application No. 13181516.9 are both incorporated herein by reference in their entireties as though fully set forth.

BACKGROUND OF THE INVENTION

The invention relates to a transdermal therapeutic system with a system support, at least one advancing element which is embedded into the system support, and at least one active substance reservoir which is elastically deformable at least in some regions and which is embedded into the advancing element, wherein, on the application side of the transdermal therapeutic system, the system support surrounds the advancing element, and the latter surrounds the active substance reservoir, and wherein the advancing element comprises a swelling body which can be expanded by means of liquid uptake.

A system of this kind is known from the post-published EP 12 158 740.6.

The problem addressed by the present invention is that of enhancing the effect of the advancing element.

SUMMARY OF THE INVENTION

This problem is solved by the features of the claims, whereby the system support is designed to be deformation-resistant at least in some regions.

BRIEF DESCRIPTION OF THE DRAWINGS

Further details of the invention will become clear from the claims and from the following descriptions of schematically depicted illustrative embodiments.

FIG. 4 shows the system with hollow needles on the advancing element;

FIG. 5 shows the system with a flexurally and torsionally rigid pressure plate;

FIG. 6 shows the system with hollow needles penetrating the active substance reservoir;

FIG. 7 shows the system as in FIG. 6 with hollow needles and semipermeable membrane;

FIG. 8 shows the system with integrated water reservoir;

FIG. 9 shows the system according to FIG. 8 after the water reservoir has been opened.

DETAILED DESCRIPTION OF THE INVENTION

Figure 1:
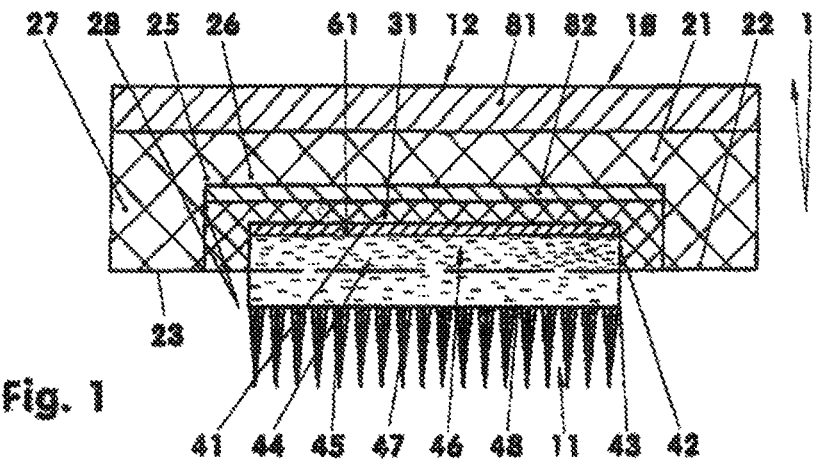
FIG. 1 shows the transdermal therapeutic system.
Figure 2:
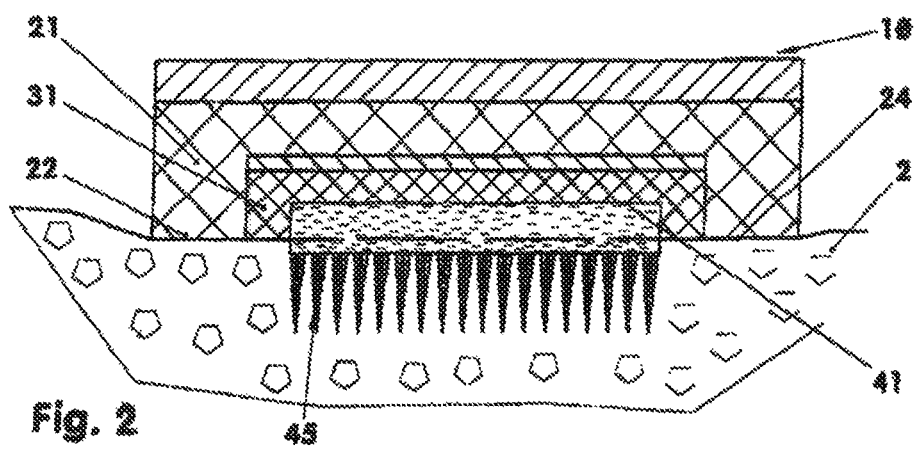
FIG. 2 shows the system after it has been placed onto the skin.
Figure 3:
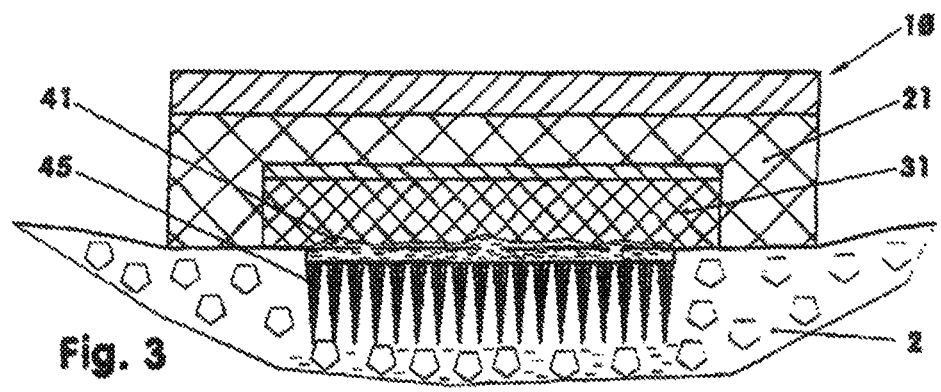
FIG. 3 shows the system during delivery of the active substance into the skin.

FIGS. 1-3 show a transdermal therapeutic system (10). Systems (10) of this kind are used to introduce liquid or liquefiable substances into the skin (2) of a patient. It has an application side (11) that can face toward the skin (2) of the patient, and a handling side (12) facing away therefrom.

The transdermal therapeutic system (10) comprises a system support (21) which can be secured on the skin (2) of the patient, for example, by means of an adhesive layer (22). This adhesive layer (22) can be free of active substances. On the bearing surface (24) facing toward the skin (2), it can be applied to a support part (23) of the system support (21). However, it is also conceivable to construct the entire system support (21) from the material of the adhesive layer (22).

In the illustrative embodiment, the side of the system support (21) facing away from the skin (2) carries a covering layer (81). In a design of the system support (21) made from the material of the adhesive layer (22), the covering layer (81) is glued to the system support (21).

The system support (21) is constructed as a concave body. It comprises a cover part (26) and wall parts (27) adjoining the latter. In the illustrative embodiment, the wall parts (27) are twice as thick as the cover part (26). In the illustrative embodiment, the thickness of the cover part (26) is more than one third of the height of the transdermal therapeutic system (10) above the bearing surface (24). The system support (21) thus has a high resistance moment against bulging of the cover part (26). In the illustrative embodiment, an additional protective layer (82) is arranged on the inner face of the cover part (26). The height of the wall parts (27) in a direction perpendicular to the bearing surface (24) is greater than two thirds of the overall height of the transdermal therapeutic system (10) above the bearing surface (24). The system support (21) thus has a high resistance moment against bending and also against torsion. The system support (21) is thus deformation-resistant, taking into consideration the flexibility that is required for wearing comfort.

The wall parts (27) and the cover part (26) form a shell (25) and delimit on five sides an interior (28) of the system support (21). The join of the wall parts (27) to the cover part (26) can be at right angles. Hollow fillets can be formed in the area of this join. However, the interior (28) can also be open in a funnel shape in the direction of the application side (11). The angle enclosed by a wall part (27) and a vertical plane is, for example, smaller than or equal to 45 degrees.

An advancing element (31) is arranged in the interior (28). In the installed state, this advancing element (31) is flush with the bearing surface (24), or it protrudes from the bearing surface (24) in the direction of the skin (2). In the illustrative embodiment, the advancing element (31) is composed of an elastically and/or plastically deformable material. The basic materials of the advancing element (31) are, for example, crosslinked polymers that contain the sodium salt of acrylic acid. The use of sodium polyacrylate or crosslinked polyacryl amides is also conceivable. These materials are hydrophilic. Depending on the composition and nature of the liquid, they are able to take up 30 times to 800 times their weight of liquid. For example, the absorbency is determined by the electrical potential difference of the material and of the liquid to be absorbed. In the illustrative embodiment, the liquid used is water. The latter can be distilled or demineralized.

The volume of the advancing element (31) increases as liquid is absorbed. For example, the increase in volume is proportional to the volume of the absorbed liquid. The advancing element (31) is therefore also designated below as a swelling body (31).

An active substance reservoir (41) is embedded in the advancing element (31). It protrudes therefrom above the bearing surface (24). The active substance reservoir (41) is bag-shaped and contains one or more active substance formulations. It is produced from an elastically deformable material.

Instead of a single active substance reservoir (41), it is also possible for several active substance reservoirs (41) to be embedded in the advancing element (31). They can be arranged alongside one another or over one another. For example, the walls (42) of the active substance reservoir (41) are semipermeable or are equipped in such a way that, for example, individual active substances are mixed together directly before being applied.

An intermediate layer (61) can be arranged between the advancing element (31) and the active substance reservoir (41). This intermediate layer (61) can be designed, for example, as a pressure plate (61) and/or a water-absorbing layer (61), or the active substance-containing layer (41) is, for example, separated from the advancing element (31) by a film (e.g. polyethylene terephthalate, abbreviated PET).

A needle carrier (43) with a multiplicity of needles (45) is also secured on the active substance reservoir (41). The needle carrier (43) and the needles (45) protrude from the bearing surface (24) on the side facing away from the system support (21). For example, the needle support (43) comprises a distributor channel (48) and connects the interior (46) of the active substance reservoir (41), filled with active substance (44), to the needles (45). The active substance reservoir (41) can also be designed without a distributor channel (48). The needle carrier (43) then forms a boundary of the interior (46) of the active substance reservoir (41).

The individual needle (45) has a length of between 10 micrometers and one millimeter. Its external diameter is between ten micrometers and 500 micrometers. In the illustrative embodiment, all the needles (45) are designed as hollow micro-needles. The diameter of the through-bore (47) is between 3 micrometers and 80 micrometers. The micro-needles (45) secured on the application side (11) on the needle support (43) can also be designed as porous needles (45) or as soluble needles (45). The mircro-needles (45) are preferably at least one of porously soluble and swellable. The needles (45) shown with a conical shape in the figures can also have a cylindrical shaft and a conical tip. The needles (45) thus connect the interior (46) of the active substance reservoir (41) to the environment (1).

It is also conceivable to arrange needles (33) on the advancing element (31) (cf. FIG. 4). These have, for example, the same internal and external dimensions as micro-needles (45). The needles (33) can also be secured on the needle support (43) outside the distributor channel (48).

During use of the transdermal therapeutic system (10), the latter is placed with the needles (45) onto the skin (2) of the patient and is pressed on until the bearing surface (24) bears on the skin (2) of the patient (cf. FIG. 2). The adhesive layer (22) affixes the skin (2) to the transdermal therapeutic system (10). The advancing element (31) can contact the skin (2) of the patient. The needles (45) are pushed into the skin (2) of the patient. On account of their short length, they pierce substantially the outer layer of skin (stratum corneum) and end outside the nerve endings of the deeper skin layers, such that the patient feels no appreciable pain during the application.

The advancing element (31) takes up moisture from the skin (2). The volume of the swelling body (31) increases (cf. FIG. 3). If appropriate, liquid can be taken up from the area below the stratum corneum via needles (33), as is shown in FIG. 4. Since the system support (21) prevents or at least greatly reduces the free deformation of the swelling body (31), the swelling body (31) can expand substantially only in the direction of the active substance reservoir (41). The elastically deformable active substance reservoir (41) is deformed and compressed. Active substance (44) is thus forced out of the interior (46) of the active substance reservoir (41) into the needle support (43) and into the needles (45). From the needles (45), the active substance (44) is conveyed into the skin (2) of the patient. As more liquid is taken up, the active substance reservoir (41) is further deformed. In this way, active substance (44) is increasingly forced into the skin (2) of the patient. During the uptake of liquid, the liquid is stored in the swelling body (31) and not released.

The delivery of active substance is ended when either the swelling body (31) is expanded to its maximum volume or when all the active substance (44) has been forced out of the active substance reservoir (41) in the direction of the skin (2).

In the embodiment in FIG. 5, the system support (21) protrudes with a stamp (29) into the interior (28). This stamp has a square cross section, for example, and delimits the advancing element (31) laterally adjoining it. In this illustrative embodiment, the for example mat-shaped advancing element (31) has a central recess (32) which engages around the stamp (29). In the view in FIG. 5, the pressure plate (61) is arranged above the active substance reservoir (41). The pressure plate (61) comprises a plate (62) with a reinforcing edge (63). In the illustrative embodiment, diagonal ribs (64) are also arranged on the top face of the plate (62) and intersect in the middle of the top face of the pressure plate (61). The pressure plate (61) thus has a torsionally rigid and flexurally rigid design. If appropriate, the pressure plate (61) can additionally be guided in a for example vertically arranged guide bolt.

During use of the transdermal therapeutic system (10), in this illustrative embodiment too, liquid is taken up from the skin surface or from the skin (2) by means of the advancing element (31). The swelling body (31) expanding as a result of the uptake of liquid presses the pressure plate (61) downward in the view in FIG. 5. The swelling body (31) is in this case guided on the system support (21) and on the stamp (29). The pressure plate (61) is moved at least approximately parallel and compresses the active substance reservoir (41). In the case of a pressure plate (61) guided, for example, by means of a guide pin, the guiding additionally prevents jamming. The active substance (44) is forced substantially uniformly out of the interior (46) into the needles (45) and into the skin (2).

FIG. 6 shows a transdermal therapeutic system (10) with additional hollow needles (34). These hollow needles (34) are arranged parallel to the needles (45) that convey the active substance (44) into the skin (2). For example, the number of the hollow needles (34) is a fifth of the number of the needles (45) carrying the active substance. The hollow needles (34), of which the tips (39) in the illustrative embodiment have the same dimensions as the needles (45) carrying the active substance, pass through active substance reservoir (41), e.g. in sealed passages (49). The hollow needles (34) pass through the advancing element (31) and, in the view in FIG. 6, bear on the protective layer (82) in the system support (21). In the area of the advancing element (31), the hollow needles (34) have passages (35) extending through their circumferential surface. In this way, the central area of the advancing element (31) is connected to the environment (1) by means of the hollow needles (34). The distance of the passage (35) from the needle tip (39) is smaller than the reciprocal value of the diameter of the cavity (37) in millimeters, multiplied by an area of 25 square millimeters. For example, if the cavity (37) has a diameter of 0.5 millimeter, the maximum distance is 50 millimeters.

During the use of the transdermal therapeutic system (10), the liquid from the skin (2) ascends through the hollow needles (34), for example by the capillary effect, and reaches the advancing element (31). The liquid entering the latter causes an additional swelling of the swelling body (31) in the areas adjoining the hollow needles (34). For example, the central portion of the active substance reservoir (41) can be compressed earlier than in the embodiment according to FIGS. 1-3.

In the view in FIG. 7, the hollow needle (34) passes through the system support (21). On the outside of the covering layer (81), for example, a semipermeable membrane (36) is arranged which closes the cavity (37) of the hollow needle (34) on the handling side (12). This semipermeable membrane (36) allows gas and/or liquid to pass from the cavity (37) to the environment (1). However, the movement of these substances from the environment (1) into the cavity (37) is blocked. Instead of the semipermeable membrane (36), a nonreturn valve, etc., can also be provided.

The function of the transdermal therapeutic system (10) shown in FIG. 7 is similar to the function of the system (10) shown in FIG. 6. The air displaced during the ascent of the liquid from the capillary (37) can here escape through the semipermeable membrane (36) into the environment (1).

FIGS. 8 and 9 show a transdermal therapeutic system (10) with an integrated liquid reservoir (71), e.g. a water reservoir (71). The water reservoir (71) is arranged in the interior (28) of the system support (21) between the advancing element (31) and the system support (21). It comprises a jacket (72), which can be torn open, for example. In the views in FIGS. 8 and 9, a lattice (73) is arranged between the water reservoir (71) and the advancing element (31). This lattice (73) is, for example, anchored in the system support (21).

On the side facing toward the water reservoir (71), the advancing element (31) carries tearing spikes (38), which are initially spaced apart from the water reservoir (71), for example by a few tenths of a millimeter.

When the transdermal therapeutic system (10) is placed onto the skin (2), the needles (45) and the active substance reservoir (41) are moved toward the system support (21). The advancing element (31) guided in the system support (21) is moved in the direction of the water reservoir (71) by the active substance reservoir (41). In doing so, the tearing spikes (38) contact the jacket (72) of the water reservoir (71) and tear the jacket (72) of the water reservoir (71) open (cf. FIG. 9). The water (75) leaving the water reservoir (71) enters the advancing element (31) and causes the latter to swell. If appropriate, the water (75) can spray into the advancing element (31). The lattice (73) here prevents an expansion of the swelling body (31) in the direction of the system support (21). The swelling body (31) compresses the active substance reservoir (41). The active substance (44) is forced out of the active substance reservoir (41) and through the needles (45) into the skin (2).

It is also conceivable to arrange tubular capillaries in the advancing element (31). Here, in addition to the conveying effect of the material of the advancing element (31), liquid can be conveyed into the central area of the advancing element (31). It is also conceivable for liquid to be guided by means of the intermediate layer (61). If appropriate, the swelling of the swelling body (31) can thus be controlled.

Of course, it is also conceivable for the various embodiments mentioned to be combined with one another.

LIST OF REFERENCE SIGNS 1 environment
2 skin
10 transdermal therapeutic system
11 application side
12 handling side
21 system support
22 adhesive layer
23 support part
24 bearing surface
25 shell
26 cover part
27 wall parts
28 interior
29 stamp
31 advancing element, swelling body
32 recess
33 needles, hollow needle
34 hollow needles
35 passages
36 semipermeable membrane, nonreturn valve
37 cavity, capillary
38 tear-open spikes
39 needle tip
41 active substance reservoir
42 walls
43 needle support
44 active substance, active substance formulation
45 needles, micro-needles
46 interior
47 through-bore
48 distributor channel
49 passages
61 pressure plate, intermediate layer, water-absorbing layer
62 plate
63 reinforcing edge
64 diagonal ribs
71 liquid reservoir, water reservoir
72 jacket
73 lattice
75 water
81 covering layer
82 protective layer

What is claimed is:

1. A transdermal therapeutic system (10) for introducing liquid or liquefiable substance into skin (2) of a patient, including a system support (21) comprising a concave body including a cover part (26) and wall parts (27) adjoining the cover part (26), the cover part (26) and the wall parts (27) in operative arrangement to form a shell (25), an interior (28) of the system support (21) is delimited on five sides by the shell (25), the system support (21) includes a support part (23) including a bearing surface (24) facing toward the skin (2) in an operative position, at least one advancing element (31) is arranged in the interior (28) of the system support (21) and is flush with the bearing surface (24) or it protrudes from the bearing surface (24) in the direction of the skin (2) in the operative position, and at least one active substance reservoir (41) which is elastically deformable at least in some regions and which is embedded into the advancing element (31), wherein, on an application side (11) of the transdermal therapeutic system (10), the shell (25) of the system support (21) surrounds the advancing element (31), and the latter surrounds the active substance reservoir (41), and wherein the advancing element (31) comprises a swelling body (31) which is expanded by liquid uptake, characterized in that the system support (21) is deformation-resistant at least in some regions.

2. The transdermal therapeutic system (10) as claimed in claim 1, characterized in that the active substance reservoir

(41) includes hollow micro-needles (45), which connect an interior (46) of the active substance reservoir (41) to the environment (1) on the application side (11).

3. The transdermal therapeutic system (10) as claimed in claim 1, characterized in that the system support (21) comprises an adhesive layer (22) at least on the application side (11).

4. The transdermal therapeutic system (10) as claimed in claim 1, characterized in that the active substance reservoir (41) comprises a liquid or liquefiable active substance formulation (44).

5. The transdermal therapeutic system (10) as claimed in claim 1, characterized in that an intermediate layer (61) is arranged between the swelling body (31) and the active substance reservoir (41).

6. The transdermal therapeutic system (10) as claimed in claim 1, characterized in that at least one hollow needle (33, 34) connects the swelling body (31) to the environment (1) on the application side (11).

7. The transdermal therapeutic system (10) as claimed in claim 6, characterized in that a semipermeable membrane (36) closes the hollow needle (34) on a handling side (12) of the transdermal therapeutic system (10) facing away from the application side (11).

8. The transdermal therapeutic system (10) as claimed in claim 2, characterized in that the micro-needles (45) are at least one of porously soluble and swellable.

9. The transdermal therapeutic system (10) as claimed in claim 2, characterized that an integrated liquid reservoir (71) is operatively arranged in the interior (28) of the system support (21) between the advancing element (31) and the system support (21), the advancing element (31) carries tearing spikes (38) which are initially spaced apart from the integrated liquid reservoir (71) until use of the transdermal therapeutic system (10) wherein the tearing spikes (38) opens the integrated liquid reservoir (71) causing the advancing element (31) to swell and forces an active substance (44) out of the active substance reservoir (41) through the micro-needles (45).

\* \* \* \* \*